(12) United States Patent
Dunne et al.

(10) Patent No.: US 9,050,428 B2
(45) Date of Patent: Jun. 9, 2015

(54) DEVICE, CARTRIDGE AND METHOD FOR DISPENSING A LIQUID

(75) Inventors: Stephen T. Dunne, Stowmarket (GB); Holger Holakovsky, Witten (DE); Alexander Bach, Essen (DE); Jens Besseler, Bingen am Rhein (DE); Manuel Krakowka, Welver (DE); Gilbert Wuttke, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 249 days.

(21) Appl. No.: 13/147,655

(22) PCT Filed: Aug. 17, 2009

(86) PCT No.: PCT/EP2009/005949
§ 371 (c)(1),
(2), (4) Date: Sep. 8, 2011

(87) PCT Pub. No.: WO2010/094305
PCT Pub. Date: Aug. 26, 2010

(65) Prior Publication Data
US 2012/0090603 A1    Apr. 19, 2012

(30) Foreign Application Priority Data
Aug. 17, 2009   (WO) ................. PCT/EP2009/005949

(51) Int. Cl.
*A61M 15/00*   (2006.01)
*A61M 11/02*   (2006.01)
*A61M 11/06*   (2006.01)
*B65D 83/62*   (2006.01)
*A61M 11/00*   (2006.01)
*B05B 11/00*   (2006.01)
*B65D 83/38*   (2006.01)
*B65D 83/48*   (2006.01)

(52) U.S. Cl.
CPC .......... *A61M 15/0065* (2013.01); *A61M 11/06* (2013.01); *A61M 15/009* (2013.01); *A61M 2202/0468* (2013.01); *B05B 11/3091* (2013.01);
(Continued)

(58) Field of Classification Search
CPC ............ A61M 15/00; A61M 15/0065; A61M 15/0086; A61M 15/009; A61M 11/06; A61M 11/007; B65D 83/48; B65D 83/62; B65D 83/386; B05B 11/3091
USPC ............. 128/200.14, 200.21, 200.22, 200.23; 222/394, 395, 402.1, 402.2
See application file for complete search history.

(56) References Cited

U.S. PATENT DOCUMENTS 4,245,788 A      1/1981   Wright
5,059,187 A *   10/1991   Sperry et al. .................. 604/290
(Continued)

FOREIGN PATENT DOCUMENTS

EP        1312417 A2      5/2003
WO    2004062813 A1      7/2004

OTHER PUBLICATIONS

International Search Report and Written Opinion for PCT/EP2009/005949 mailed Jan. 20, 2010.

*Primary Examiner* — Justine Yu
*Assistant Examiner* — Timothy Stanis
(74) *Attorney, Agent, or Firm* — Michael P. Morris; Mary-Ellen M. Devlin

(57) ABSTRACT

A device, cartridge and method for dispensing a liquid, preferably a drug, are proposed. The liquid is pressurized in a cartridge to a first lower pressure and, then, pressurized in doses by a pump to a second higher pressure. A valve arranged between the cartridge and the pump is normally closed and/or opened only temporarily. Thus, evaporation and dripping of liquid can be avoided or minimized.

31 Claims, 16 Drawing Sheets

Figure 1:
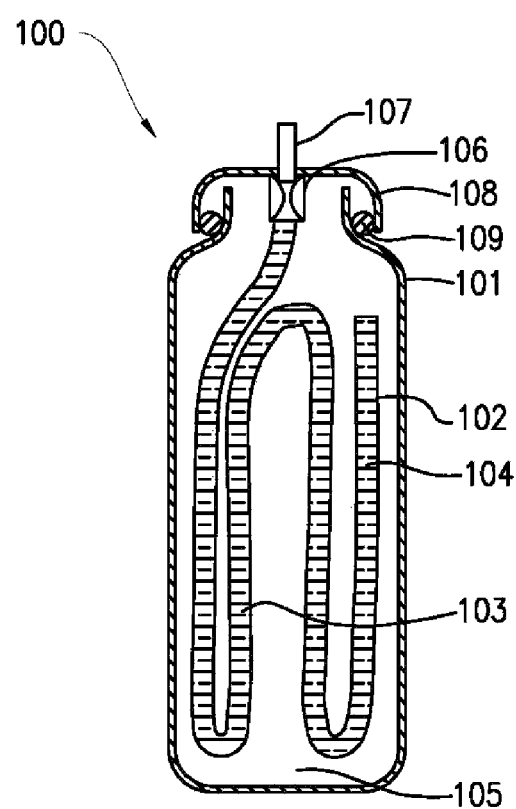

(52) U.S. Cl.
CPC .............. *B65D 83/386* (2013.01); *B65D 83/48* (2013.01); *B65D 83/62* (2013.01); *A61M 11/007* (2014.02)

(56) References Cited

U.S. PATENT DOCUMENTS

| | | | |
|---|---|---|---|
| 6,427,682 B1 * | 8/2002 | Klimowicz et al. ...... 128/200.16 |
| 6,978,916 B2 * | 12/2005 | Smith ........................ 222/402.2 |
| 6,988,496 B1 * | 1/2006 | Eicher et al. ............. 128/200.14 |
| 7,341,208 B2 | 3/2008 | Peters et al. |
| 2005/0098172 A1 * | 5/2005 | Anderson ................ 128/200.23 |
| 2005/0247305 A1 * | 11/2005 | Zierenberg et al. ....... 128/200.14 |
| 2007/0090205 A1 * | 4/2007 | Kunze et al. ................... 239/338 |
| 2007/0137643 A1 * | 6/2007 | Bonney et al. ........... 128/200.23 |
| 2009/0166379 A1 * | 7/2009 | Wright et al. .................... 222/80 |

\* cited by examiner

DEVICE, CARTRIDGE AND METHOD FOR DISPENSING A LIQUID

The present invention relates to a device for dispensing, in particular atomizing, a liquid, preferably an inhaler, with a preferably pre-inserted cartridge, to a cartridge and to a method for pressurizing and dispensing a liquid.

The present invention relates in particular to the dispensing of a liquid which consists of or contains a medicament, a drug formulation or an inhalation formulation. The liquid is preferably atomized or dispensed as a spray or aerosol by means of a device, such as an inhaler or the like. Preferably, the cartridge forms a reservoir of the inhaler for multiple doses of the liquid and the inhaler comprises a pump for pressurizing one dose after the other taken from the cartridge and for discharging the respective dose of liquid in particular via a nozzle to atomize the liquid to form the spray or aerosol.

U.S. Pat. No. 5,662,271 A and GB 2,251,898 A describe a gas-free metered dose inhaler comprising a piston and cylinder arrangement where a liquid drug is pressureized and forced through an atomizing nozzle at high pressure. The inhaler further includes a non-return valve connecting the cylinder to a container for storing the liquid drug. Three types of containers are described, namely a collapsible bag, a spring-loaded piston and cylinder arrangement, and a long open ended tube.

All three types of containers have problems with storing the liquid drug. The liquid is transferred from the collapsible bag by suction from the cylinder when the piston is retracted. The bag needs an under pressure within to collapse properly which causes gas bubble formation within the bag. To minimize and/or eliminate this problem, a dip tube and overfilling of the bag is needed to prevent the gas in the bubble entering the cylinder. The long tube system also requires an under pressure to work and requires an open end to allow air flowing in to balance the pressure. Evaporation can take place from this open end. The spring/piston/cylinder arrangement has an over pressure to eliminate gas bubbles, but can lead to liquid leakage via the nozzle of the inhaler.

All three types or systems need to be sealed in vapour proof canisters during storage or shell life to minimize drug evaporation or evaporation of any other component, e.g. the solvent. Prior to use the container needs to be inserted into the inhaler where a hole is pierced to allow air flowing in, and to be connected to the cylinder via a rupturable sealed connector. During use which may last up to three months some evaporation always takes place, because the container is permanently connected through the cylinder and open nozzle. Evaporation can take place from the nozzle and through the walls of the container and venting hole in a canister surrounding the container. Because of stability issues, only a few types of plastic may be used to make the container for any one drug solution. It is often difficult to find a material which is stable and has a low vapour transmission rate. This problem is much worse for volatile liquids such as ethanol based solutions.

Another problem with the above inhaler and container types is that the inhaler need to be primed (operated to fill the pump and fluidic connections with liquid), wherein often up to six puffs (operations) are needed until a full dose of liquid is delivered.

The present invention relates in particular to a cartridge (reservoir) for an inhaler for dispensing liquid by means of a pump, in particular of a piston/cylinder arrangement, and/or preferably a gas-free metered dose inhaler and/or an active inhaler.

The present invention relates in particular to an active inhaler such as an inhaler sold under the brand name "Respimat" shown in WO 2007/125577 A1. The inhaler has a pre-inserted cartridge as a reservoir containing a liquid, which is to be atomized. The inhaler comprises a pressure generator (pump) with a drive spring for metering and pressurizing the liquid. A capillary tube is inserted into the cartridge to fluidically connect the cartridge permanently to the pressure generator. The cartridge does not comprise any valve for fluidically connecting the cartridge to the inhaler. The pressurized liquid is discharged via a nozzle so that the liquid is atomized and discharged as a spray or aerosol.

Object of the present invention is to provide a device, preferably an inhaler, for dispensing a liquid and a method for dispensing a liquid, wherein priming can be eliminated or minimized and/or wherein forming of gas bubbles can be minimized and/or wherein it can be minimized or eliminated any under pressure acting on the liquid in the cartridge when liquid is delivered from the cartridge into the device or inhaler.

The above object is achieved by a device according to the present invention by a cartridge as described herein or by a method as described herein. Preferred embodiments are also described herein.

One aspect of the present invention is to combine a pump with a cartridge, wherein the cartridge comprises pressurized liquid and a valve, wherein the pump is fluidically connected or connectable to the valve and the pressure pushes the liquid out of the cartridge through the valve into the pump when the valve is open. The valve is normally closed and/or opened only temporarily. This leads to some advantages. The pressurization of the liquid in the cartridge facilitates the filling of the pump with liquid, in particular when using the pump for the first time or after longer periods of non-use. Thus, priming can be avoided or at least minimized. Further, undesired evaporation can be avoided or at least minimized due to the closure of the valve between the output or removal of one dose of liquid after the other from the cartridge, i.e. from a reservoir formed by the cartridge. Moreover, undesired leaking or dripping of liquid out of the pump or from an associated nozzle can be avoided or at least minimized due to the closure of the valve between the removal of doses of liquid from the cartridge and/or during (longer) shelf storage, longer periods of non-use or the like. In addition, the first pressurizing in the cartridge avoids any under pressure acting on the liquid in the cartridge and facilitates removal of liquid from the cartridge.

According to another aspect of the present invention the liquid is pressurized in the cartridge to a first lower pressure and, then, by means of the pump to a second higher pressure. In particular, all liquid is pressurized in the cartridge to the first lower pressure, but only one dose of liquid after the other is pressurized to the second higher pressure. Preferably, the pressurization to the second higher pressure takes place only before dispensing the respective dose of liquid, i.e. just before actual use. Alternatively or additionally, the valve connecting the reservoir of liquid, i.e. a storage means for the liquid or the cartridge, with the pump is opened only temporarily to fill the pump. Thus, the same advantages as already mentioned above can be achieved.

According to a further aspect of the present invention, a cartridge is proposed which comprises a storage means for the liquid, a valve and pressurizing means to pressurize the liquid. The valve has two closing positions and is open between these closing positions. The pressurizing means pushes the liquid out through the valve when the valve is open, i.e. between the two closing positions. In particular, the valve is continuously open and, thus allows complete filling of an associated (metering) pump, device or inhaler. Preferably, the valve is controlled by a suction and/or pump stroke of the pump, device, inhaler or the like. This allows a very simple construction. In particular, the valve is normally closed and/or opened temporarily. Preferably, the valve closes respectively when the pump, device or inhaler or the like is in the activated or cocked state or in the non-activated or non-cocked state. Thus, undesired evaporation can be avoided or at least minimized. Further, undesired leaking or dripping of liquid out of the pump from an associated nozzle or the like can be avoided or at least minimized.

Preferably, the cartridge is pre-inserted and/or pre-connected to the associated device/inhaler and/or its pressurizing means or pump. This largely eliminates any priming puffs or operations.

The valve is preferably a continuous flow aerosol valve. Such valves have a spring loaded stem or (female) valve member which can be pushed into the valve to open the valve. These valves can be built using a variety of sealing materials and are known having very long leak-free shelf lives.

The valve stem or (female) valve member is preferably permanently connected to the associated device, inhaler, pump means, cylinder or the like and/or via a non-return valve.

A canister of the cartridge may be pressurized with liquefied gases or permanent gases such air in order to pressurize the liquid.

According to another aspect a best method of filling the cartridge or container and pressurize the canister is as follows:
the valve and the storage means or container (tube, bag, piston or the like) are sealingly mounted e.g. by crimping or other means onto the canister. The liquid is forced into the storage means or container via the valve. Because the canister is sealed, the canister is pressurized as the liquid goes in or expands into or compresses the gas or air in the canister.

The storage means or container or cartridge may be over filled by a small percentage, such as 10 to 50%. This ensures that an over pressure is always present while there is liquid left.

Alternatively or additionally to the over filling, the cartridge or storage means can be filled with liquid and/or sealed under low temperature, so that the increase to room temperature leads to or supports the desired over pressure.

Because the liquid is pressurized priming of the device or inhaler or any other device is minimized. The (first lower) pressure required is low and preferably between 1 and 500 kPa, in particular between 1 and 200 kPa or 1 and 100 kPa. This is to prevent liquid escaping under pressure via a nozzle of the device when the device or inhaler is cocked or activated.

In the present invention all pressure values mean the pressure over the atmosphere, i.e. the gauge pressure.

The storage means or container may be filled after or prior to being sealed or crimped to the outer canister.

In another embodiment, the liquid may be stored directly in the outer canister eliminating the need for a separate or additional storage means such an inner bag. In this case, the valve may be connected to a dip tube for upright cocking. The dip tube may be of a flexible type allowing for 180 degree cocking.

The valve may be used with a dip tube that may be of the 360 degree ball valve type which operates at all cocking orientations.

The valve may have a dip tube connected to it in which case the device, inhaler, pump or the like must be cocked while in the upside position (mouthpiece up) or may not have a dip tube or the like in which case the device must be cocked in the upside down position (mouthpiece down).

As already mentioned, the valve may be a 360 degree type valve that has a dip tube and second entry in the valve body with ball valve for 360 degree operation in which case the device, inhaler, pump or the like may be cocked in any position.

The canister may be pressurized with liquefied gases or permanent gases such as air.

If the liquid contents are volatile such as ethanol, the contents may not need to be pressurized. However, for water-based products some pressure is preferred.

In another embodiment, the preferably un-pressurized canister—but also the pressurized canister after discharge of some liquid—may have a non-return valve or any other second valve to allow air to flow into said canister to prevent pressure reduction or under pressure in the canister as liquid contents are removed. The non-return valve or second valve may be sealed with foil to prevent evaporation during storage. Then, said foil is ruptured during the first use, stroke or cocking of the device, inhaler, pump or the like.

The present invention also provides a preferred best method of filling the storage means/container and pressurizing the canister as follows:
the valve (and dip tube) are sealingly mounted by crimping or other means onto the canister. The liquid is forced into the storage means or container via the valve. Because the canister is sealed, the air or any other gas in the canister is pressurized as the liquid goes in the air or gas in the canister.

Because the liquid is pressurized, priming of the device, inhaler, pump or the like can be minimized or even avoided.

As already mentioned, the pressure required is low and preferably between 1 and 500 kPa. This is to prevent liquid escaping under pressure via the nozzle when the device, inhaler or pump is cocked.

When the device, inhaler, pump or the like is cocked, the cartridge or canister may move, in particular away from a part of the device, the pump, the cylinder or the like. The bottom or base of the cartridge or canister may be or come in contact with a bottom part, case or housing of the device during said movement, whereby the valve may be opened or the valve stem or valve member may be forced into a valve body opening so that the valve opens and allows liquid to flow into the device, inhaler, pump or the like. In particular the valve or valve stem/valve member has a stroke less than the stroke of staid movement of the cartridge or canister or less than the stroke of the inhaler or pump or a pump piston, a control means or a second spring or any other biasing means or counter-bearing means may be used or inserted between the cartridge or canister on one hand and the bottom part, case or housing of the device, inhaler, pump or the like on the other hand.

Preferably, the valve is opened only temporarily and/or normally closed.

In a further aspect of the present invention, the valve is closed or closes automatically at the end of the cocking stroke and/or in the cocked state of the device or inhaler to prevent liquid from leaking out the cartridge and/or device/inhaler and/or between removal of doses of liquid from the storage means or cartridge. This is preferably achieved by control means controlling opening and/or closing of the valve.

The control means acts preferably on a side of the cartridge opposite to the valve or to an outlet of the cartridge or on a bottom of the cartridge. This allows a compact construction and/or realization of the control means in existing constructions.

Different realizations or constructions of the control means will be explained in the description of the drawings.

In the present invention, the term "cocked" has to be preferably understood in the sense that a device is set in a position ready for use or discharging the liquid or is activated.

The different embodiments, aspects and features of the present invention mentioned above and/or explained or described in the following may be realized to independently from each other or in any combination thereof. The cartridge may also be claimed independently from a device/inhaler.

Devices according to the present invention are in particular inhalers, but also other spraying devices for atomizing a liquid, in particular a drug or the like. The following description focuses on inhalers as preferred devices. However, this applies preferably also for other spraying devices or the like.

Figure 2:
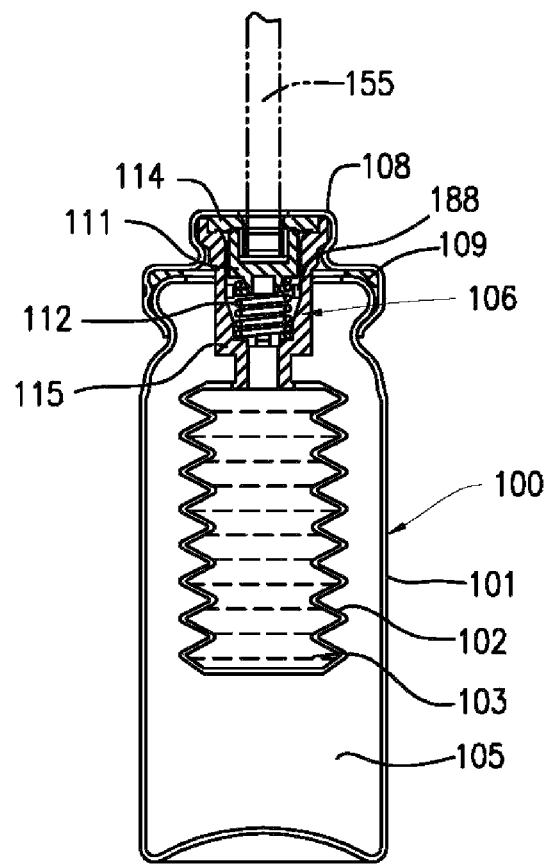
Figure 3:
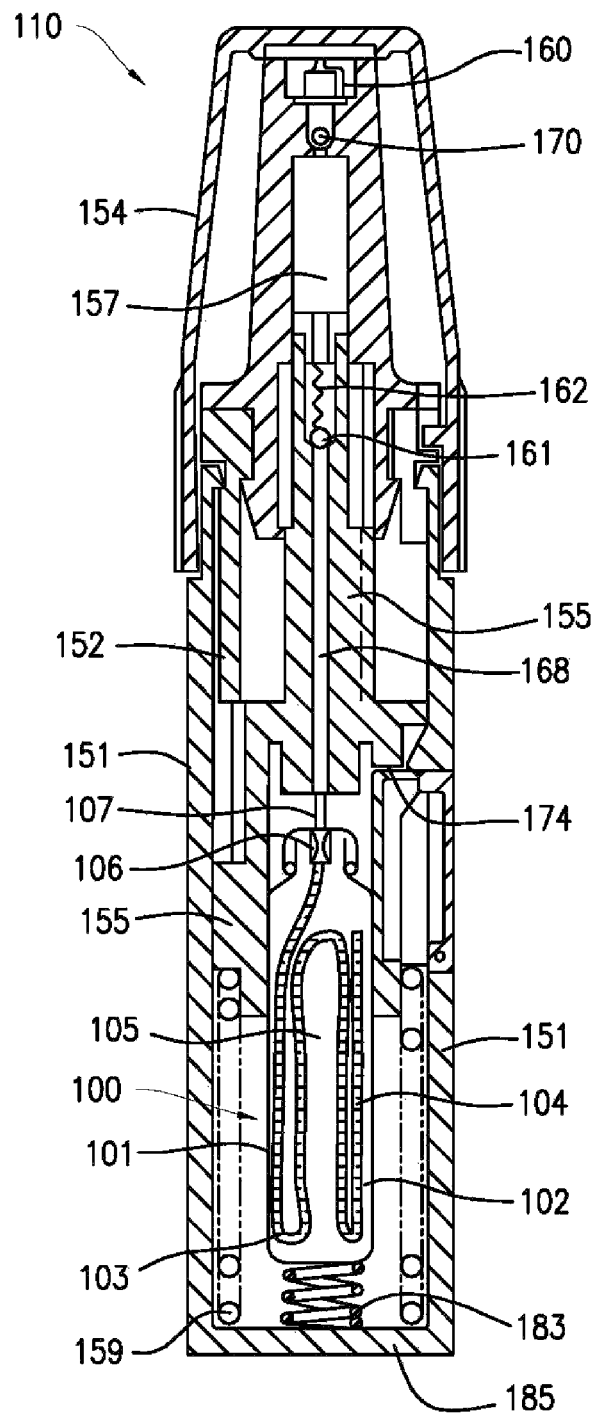
Figure 4:
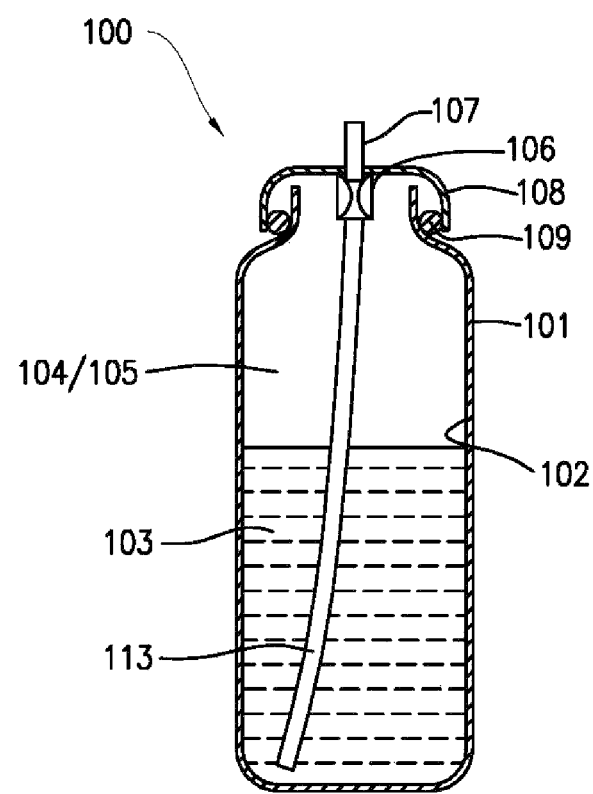
Figure 5:
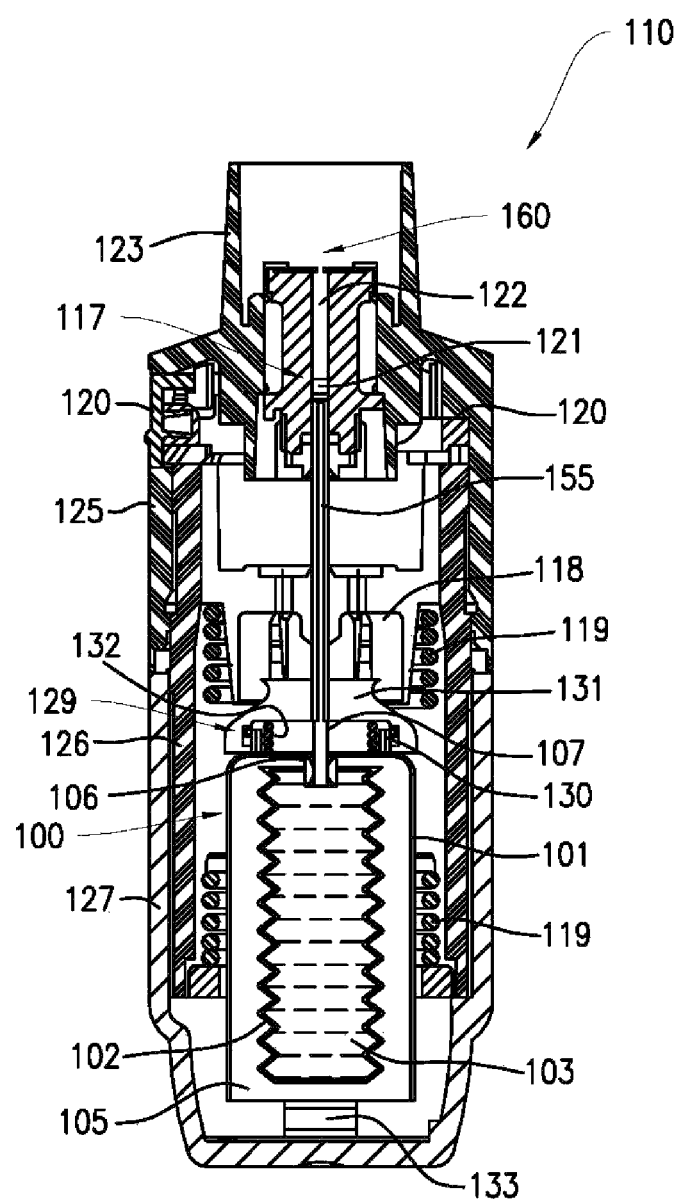
Figure 6:
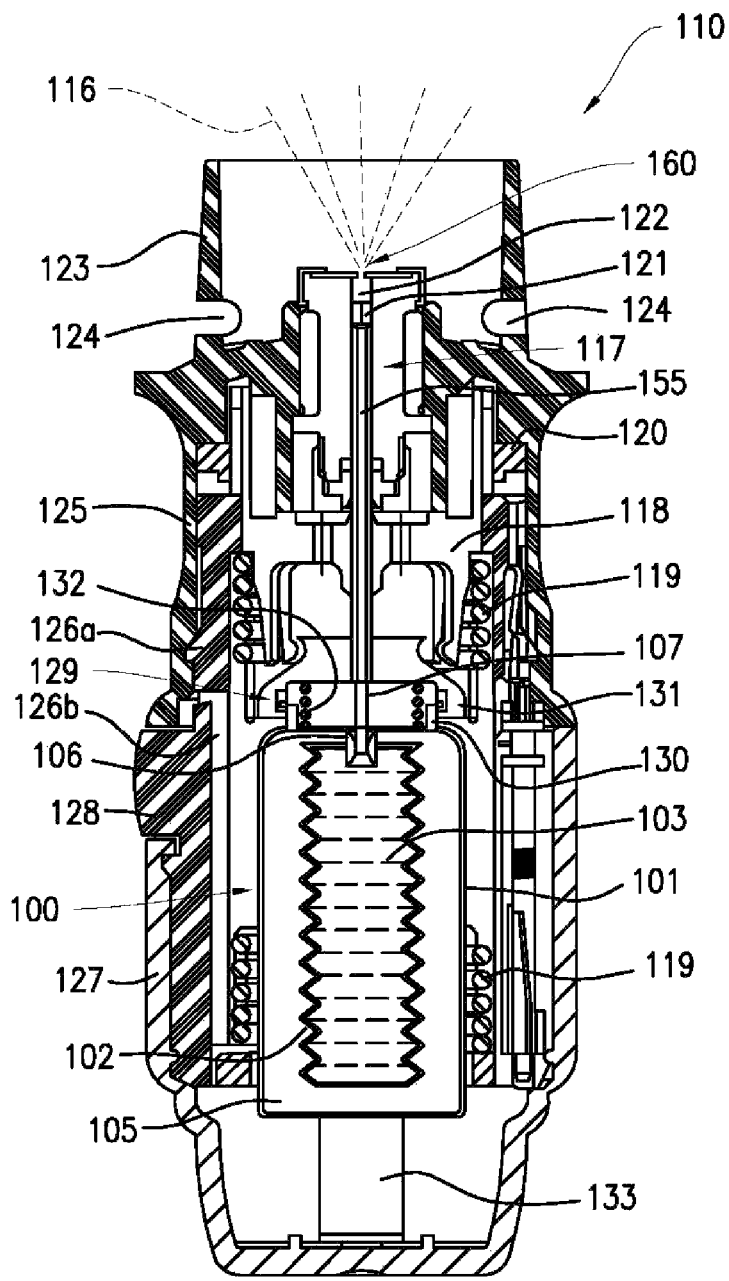
Figure 7:
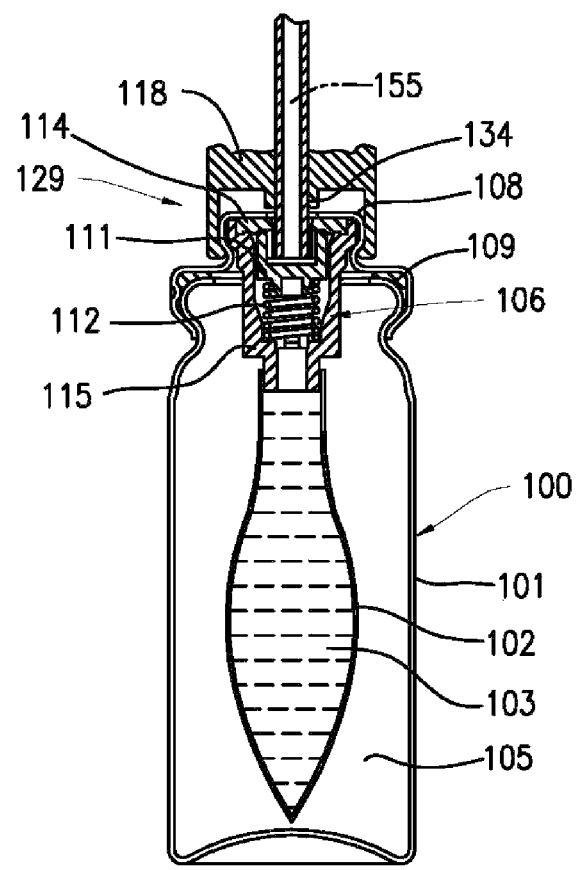
Figure 8:
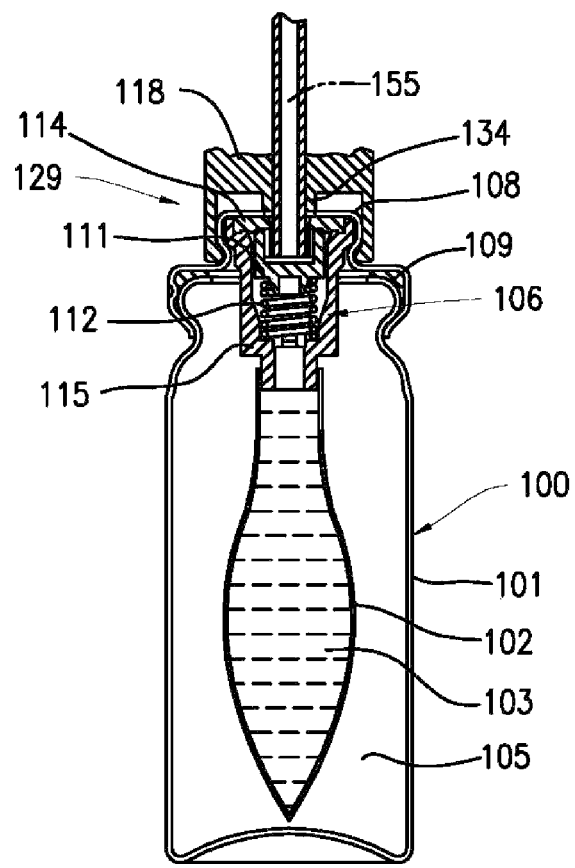
Figure 9:
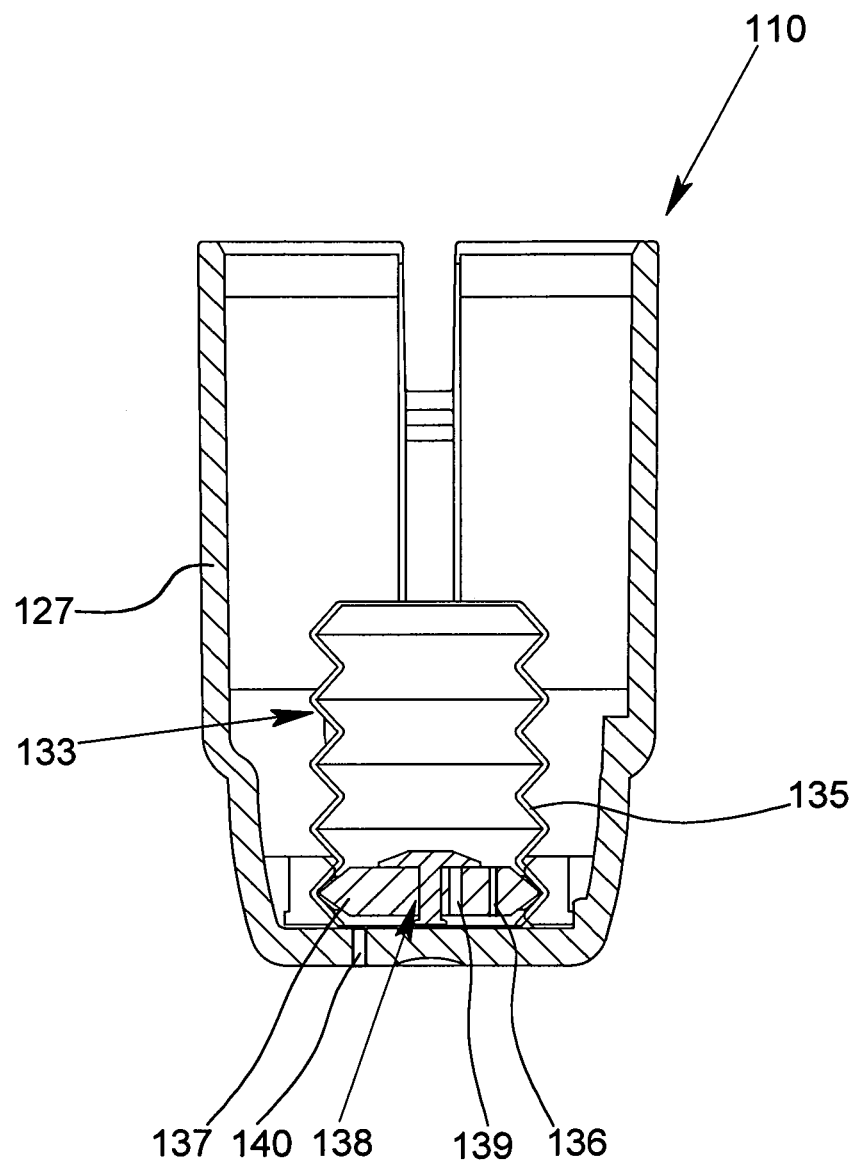
Figure 10:
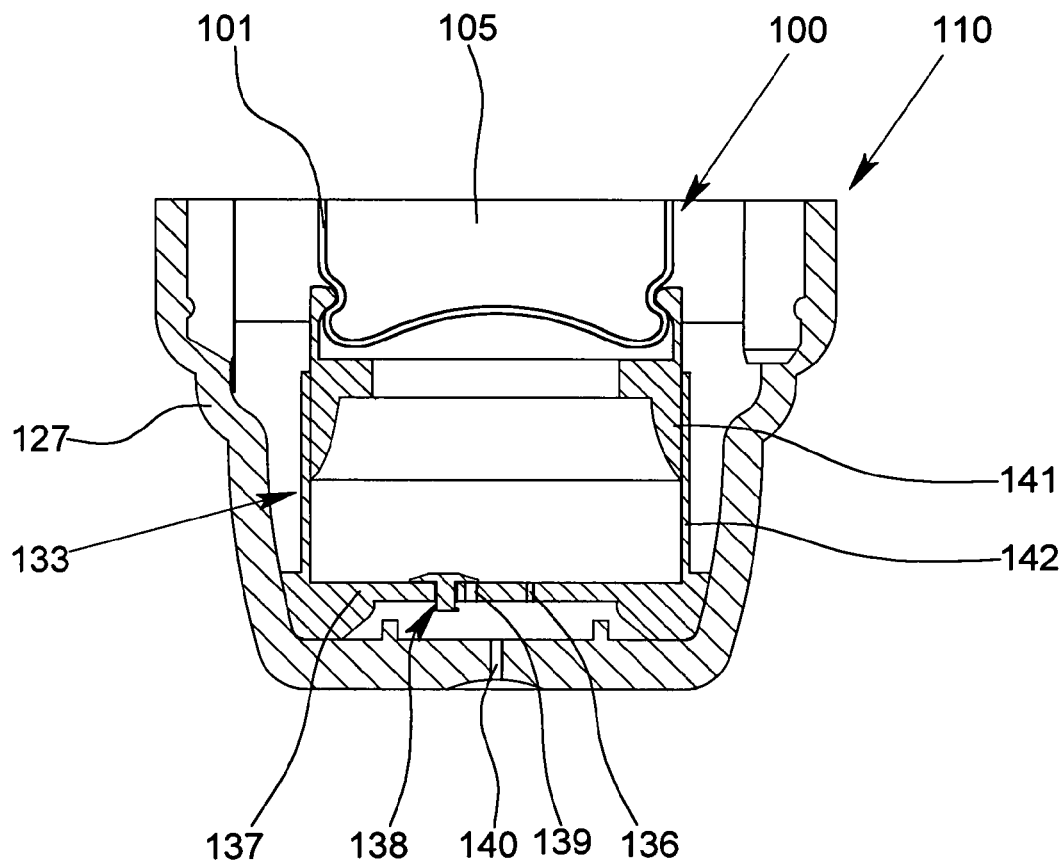
Figure 11:
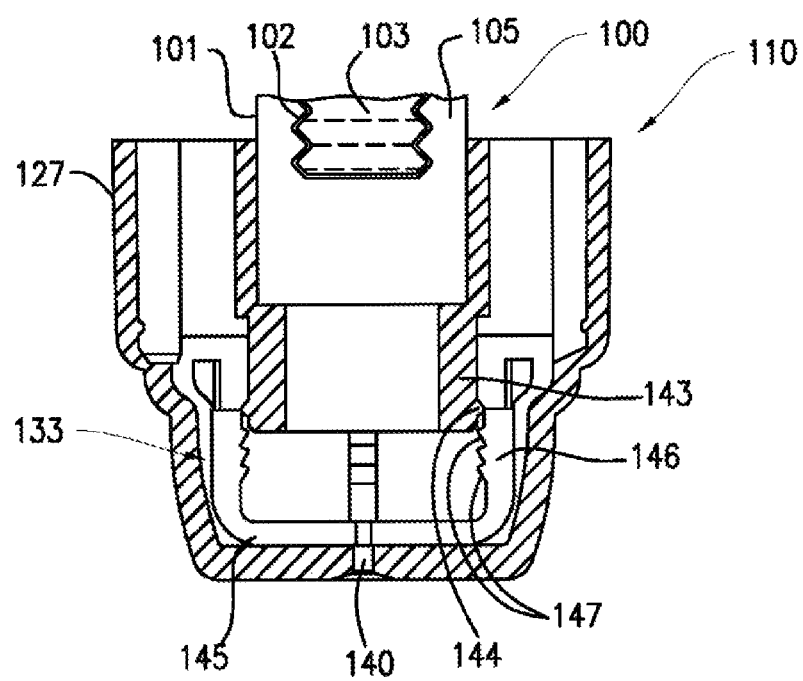
Figure 12:
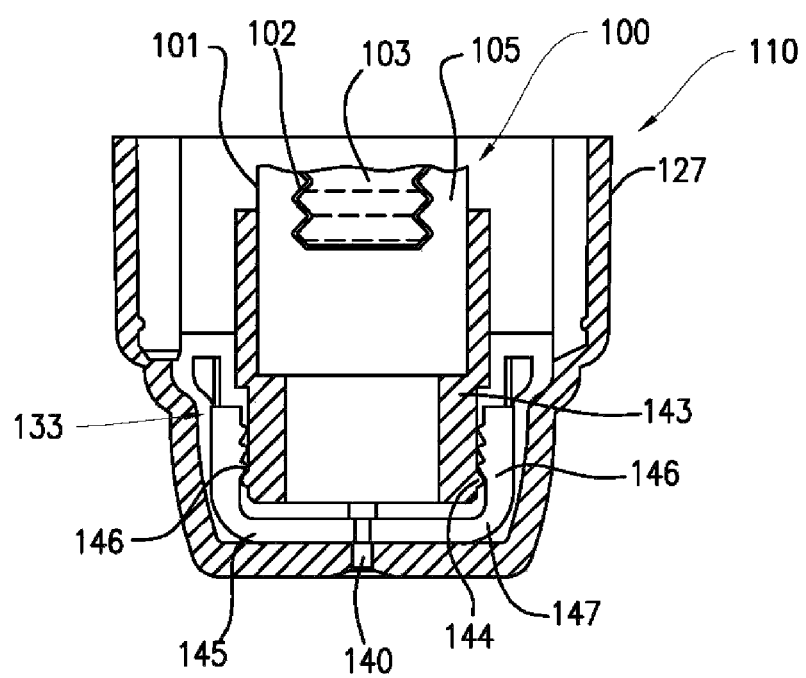
Figure 13:
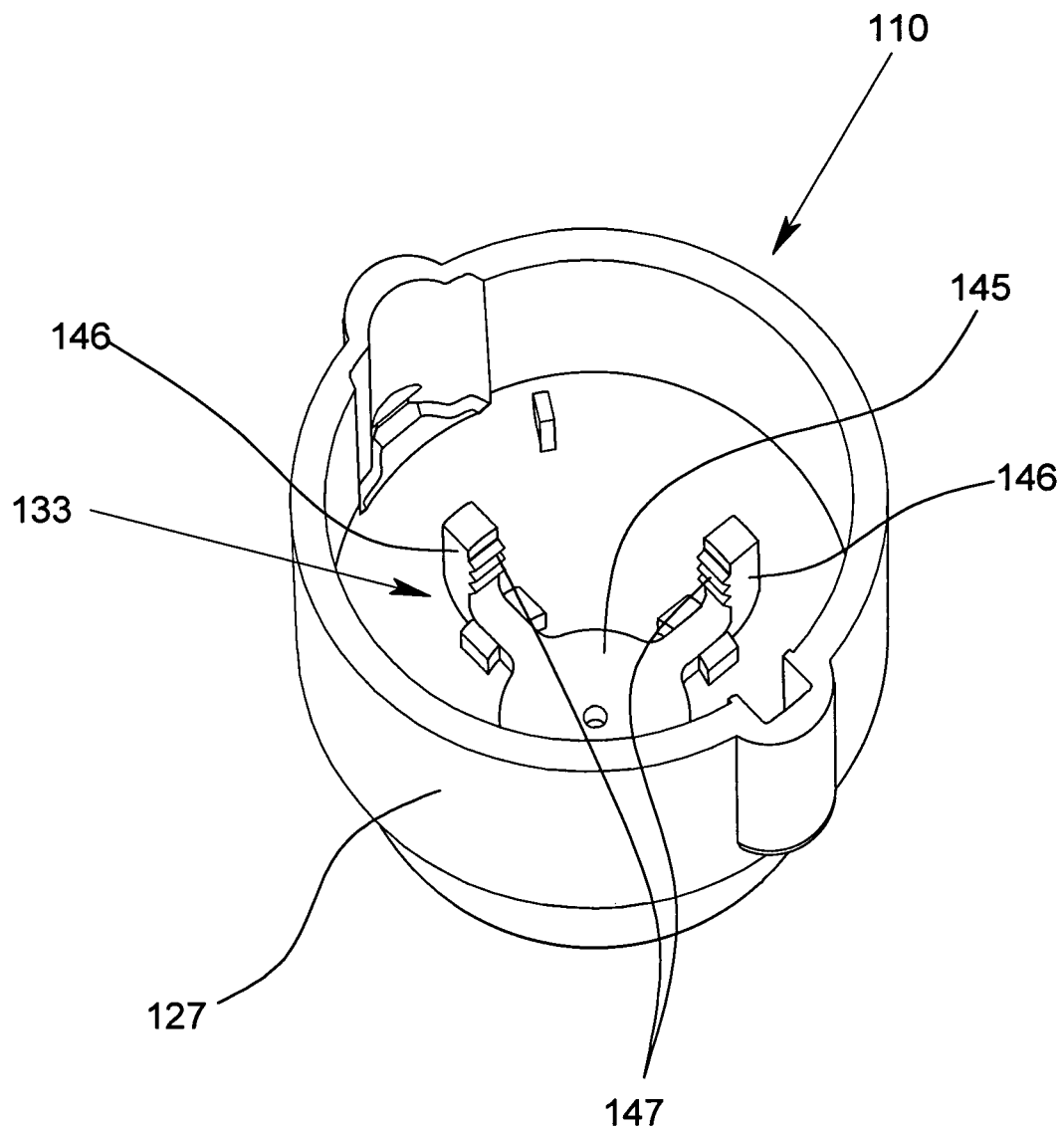
Figure 14:
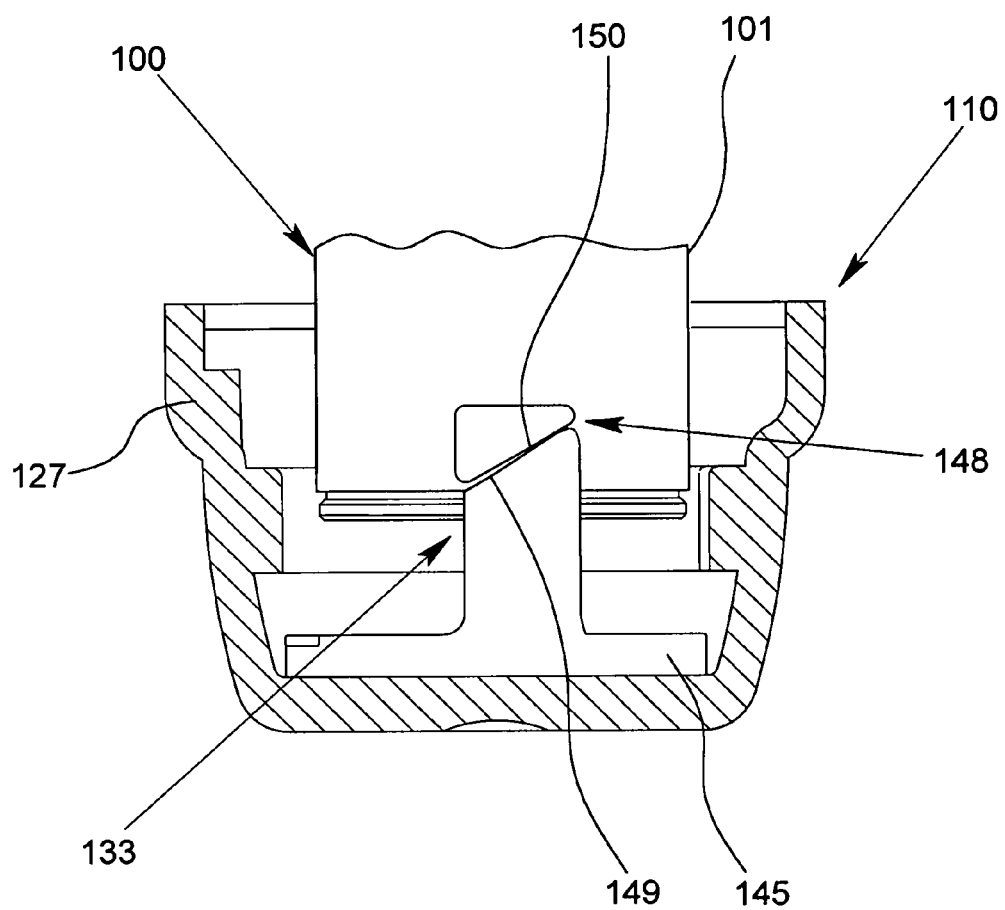
Figure 15:
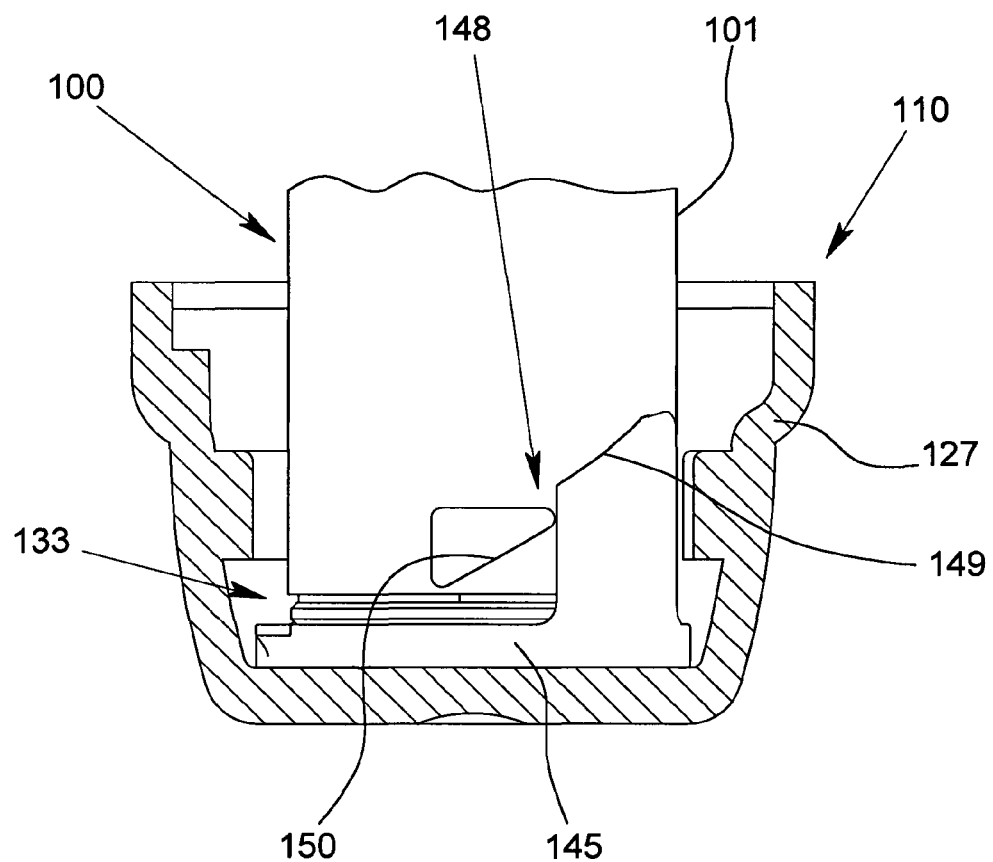
Figure 16:
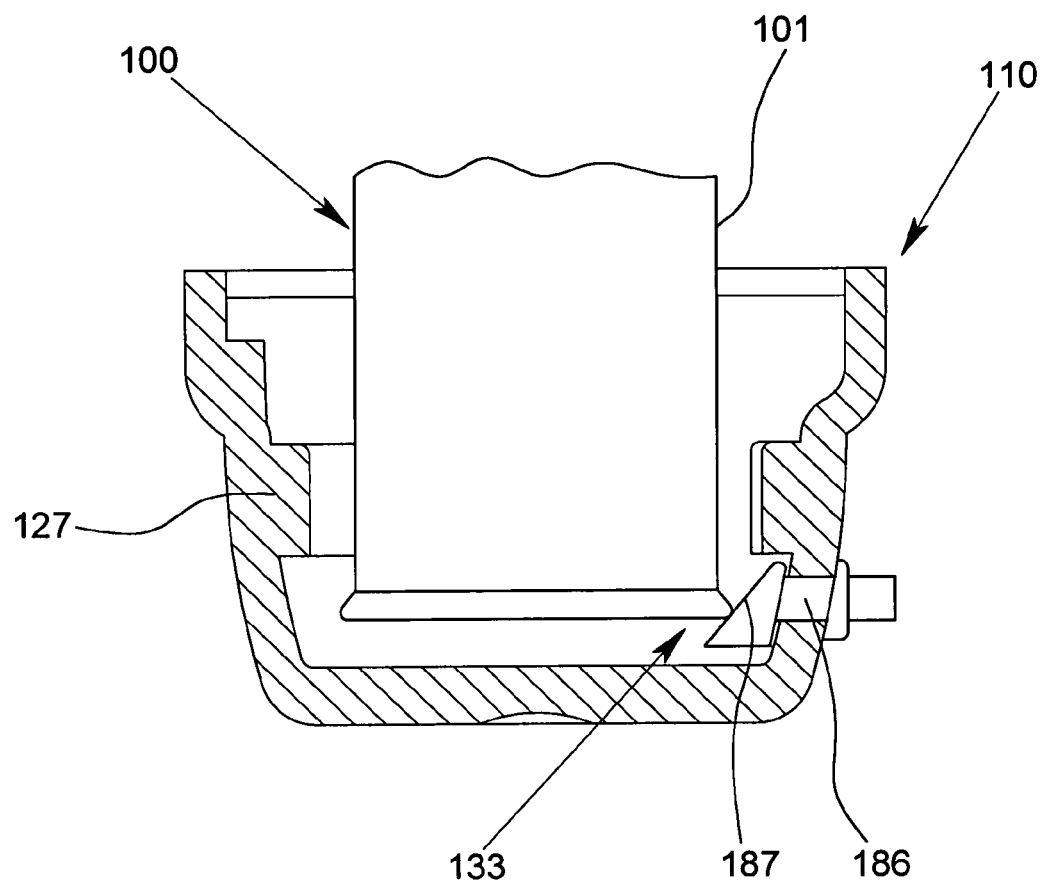

Further aspects, features, properties and advantages of the present invention are described in the claims and the subsequent description of preferred embodiments with reference to the drawing. There are shown in:

FIG. 1 a schematic section of a cartridge according to the present invention;

FIG. 2 a schematic section of a further cartridge according to the present invention;

FIG. 3 a schematic section of an inhaler with the cartridge of FIG. 1 according to the present invention;

FIG. 4 a schematic section of another cartridge according to the present invention;

FIG. 5 a schematic section of another inhaler in the tensioned, activated or cocked state; and FIG. 6 a schematic section, rotated by 90° compared with FIG. 5, of the inhaler in the non-tensioned or discharged state;

FIG. 7 a schematic section of a connection part of a cartridge mounted in an inhaler with closed valve;

FIG. 8 a schematic section of the connection part of a cartridge mounted in an inhaler with opened valve;

FIG. 9 a schematic section of a bottom part of the inhaler with a control means for controlling the valve of the cartridge;

FIG. 10 a schematic section of a bottom part of the inhaler with another control means for controlling the valve of the cartridge;

FIG. 11 a schematic section of a bottom part of the inhaler with a further control means for controlling the valve of the cartridge in the non-tensioned or discharged state;

FIG. 12 a schematic section of a bottom part of the inhaler with a further control means for controlling the valve of the cartridge in the tensioned, activated or cocked state with closed valve;

FIG. 13 a perspective view of the bottom part with a control member of the further control means;

FIG. 14 a schematic section of a bottom part of the inhaler with another control means for controlling the valve of the cartridge in an intermediate state;

FIG. 15 a schematic section of a bottom part of the inhaler with of the control part means in an activated or cocked state with closed valve; and FIG. 16 a schematic section of a bottom part of the inhaler with of a still further control means for controlling the valve of the cartridge.

In the Figures, the same reference numbers are used often for identical or similar parts, even if a repeated description is omitted. In particular identical or corresponding advantages and properties then also result or may be achieved.

FIG. 1 shows in a schematic section a cartridge 100 according to a first embodiment of the present invention. The cartridge 100 comprises a preferably rigid and/or outer canister 101 and a storage means 102, here a long tube, within the canister 101. The tube can have an open or a closed end.

However instead of or in addition to the tube, the storage means 102 can comprise or be formed by a bag as schematically shown in a second embodiment according to FIG. 2, bellows (preferably with closed end), any cylinder piston arrangement, a rigid container, the canister 101 itself or an inliner within the canister 101 or cartridge 100 or the like. The storage means 102 is preferably a collapsible or flexible bag.

Preferably, the storage means 102 is arranged within the canister 101 or cartridge 100, but it can also form (partially) any outer housing or the canister 101 or the like of cartridge 100.

The storage means 102 is preferably flexible and/or collapsible. However, the storage means 102 could also be rigid or not collapsible.

The storage means 102 or tube or bag is preferably made of plastic, foil, laminated foil, a compound or the like. Preferably, a material with a metallic, in particular aluminum, layer or foil is used to from the flexible wall of the storage means 102.

The canister 101 forms preferably an outer, rigid and/or preferably essentially cylindric housing of the cartridge 100 or storage means 102.

The storage means 102 contains liquid 103 and optionally preferably a gas or air space 104 (here only in the tube in the first embodiment).

The cartridge 100 and/or storage means 102 form a reservoir for the liquid 103, in particular multiple doses of the liquid 103.

The liquid 103 is or contains or includes a medicament, a drug formulation or an inhalation formulation.

Preferably there is a (further) gas or air space 105 within the cartridge 100 or canister 101 or any other means, in particular to pressurize the liquid 103 in a first step.

The gas or air in space 104 and/or 105 is preferably pressurized. The gas or air space 104/105 forms a pressurizing means to pressurize the liquid 103.

The storage means 102, tube or bag is connected to a (first) valve 106, which has preferably a stem 107 (see FIG. 1) or any other actuation or valve member for operating or actuating the valve 106, e.g. a female valve member 111 as shown in FIG. 2 according to a second embodiment.

The valve 106 is sealingly mounted preferably with a tap or valve cup 108 (e.g. having a diameter of 17 mm) and/or a seal 109 on canister 101 and/or preferably by crimping and/or in any other suitable manner.

To open the valve 106, the stem 107 or valve member 111 is depressed or toggled sideways. When the valve 106 is open, the pressurized gas or air pushes the liquid 103 out. The valve 106 or stem 107 or valve member 111 is preferably connected (as indicated by a tube or piston 155 in FIG. 2) or connectable via a connector or the like to a spray system, device, inhaler, pump, device cylinder, in particular via a non-return valve (not shown).

The shown valve 106 is preferably a continuous flow aerosol valve.

Preferably, the stem 107 or valve member 111 is biased by means of a spring 112 (shown in FIG. 2) or the like into the closed position where the valve 106 is closed.

In the second embodiment shown in FIG. 2, the valve 106 comprises a sealing 114, e.g. in the form of an annular ring or the like, against which the valve member 111 is biased by spring 112 in order to close the valve 106. When the valve member 111 is depressed or spaced from the sealing 114, the valve 106 opens and liquid 103 can be outputted.

In the shown embodiment, the valve 106 comprises a housing 115 which is mounted to or held by the cup 108 or any other suitable member. The housing 115 is connected with the cup 108, e.g. by crimping the cup 108 over a respective part of the housing 115 or in any other suitable manner.

Preferably, the housing 115 supports the sealing 114 and/or holds it against the cup 108. However, other constructional solutions are possible as well.

Preferably, the valve member 111 and the spring 112 are arranged within the housing 115, e.g. in a chamber fluidically connected with the storage means 102, bag or the like.

In the shown embodiment the storage means 102 is connected with the valve 106, in particular with the housing 115, preferably liquid- and preferably gas-tight.

A large number of gasket and/or plastic materials can be used in or for the valve 106, in particular such that the materials do not react with the liquid 103. The valve stem 107 or valve element may be made of metal, i.e. aluminum or stainless steel.

FIG. 3 shows in a schematic section an inhaler 110 or any other spray system, here also called device, with the preferably pre-inserted or installed and/or pre-connected cartridge 100 according to the present invention, in particular with the cartridge 100 according to the first embodiment.

The device/inhaler 110 has a body 151 with a piston 155 with a connecting element or tube 168 (fluidically) connecting the valve 106 or valve stem 107 of the valve 106 of the cartridge 100 in particular to a pump or cylinder 157 of the device/inhaler 110. In particular, the inhaler 110 comprises a pump—here formed by the axially moveable piston 155 and the cylinder 157—to deliver and pressurize liquid 103 from the cartridge 100.

The piston 155 has preferably a (first) non-return valve in particular at its top, in particular formed by a ball 161 and, if necessary, an associated spring 162.

The piston 155 is spring-loaded by spring 159 (in FIG. 3 preferably in the upward direction). The back and forth movement of the moveable piston 155 is used to suck liquid 103 via the valve 106, stem 107 or valve member, connecting element or tube 168 and/or the non-return valve into the cylinder 157 (suction stroke) and to pressurize the liquid 103 in the cylinder 157 (discharge stroke) so that the pressurized liquid 103 is discharged via an optional second non-return valve 170 connecting the cylinder 157 to an atomizing nozzle 160, in particular a mechanical break-up nozzle.

The device/inhaler 110 is shown in the cocked position with compressed spring 159 and with piston 155 fully retracted at which position the valve 106 is may be open.

A force produced by an optional biasing means, here a spring 183, of the device/inhaler 110 pushes the cartridge 100 or canister 101 or valve 106 up against the cylinder 155, connecting element or tube 168 and/or valve stem 107 so that the valve 106 is opened. In this (open) position, the liquid drug (liquid 103) can flow into the cylinder 157 forming a metering chamber. It has to be noted that the tube 168 and cylinder 157 are shown empty, i.e. without liquid 103, in FIG. 3.

When the device/inhaler 110 is fired (operated), e.g. by unlocking a locking element 152—after opening or removing cover 154—the valve 106 closes as the cartridge 100 or canister 101 moves away from spring 183 or from the lower or bottom part 185 of the inhaler 110, in particular due to the discharge stroke of the piston 155 (here upwards) preferably due to the force of spring 159.

Preferably, the valve 106 is opened only temporarily and/or is closed automatically. This will be explained later in more detail.

Preferably, the valve 106 or stem 107 or valve member 111 is permanently connected to the device/inhaler 110, connecting element or tube 168, pump (here formed by the piston 155/cylinder 157/arrangement or the like).

The biasing means (here spring 183) compensates preferably any tolerances and/or the difference between the small stroke required to open valve 106 and the preferably larger suction and discharge stroke of the pump or inhaler 110, here piston 155. However, other constructional solutions are possible as well.

In the following, some other embodiments will be described. The previous aspects and features shall apply preferably in a similar manner and/or additionally, even if a respective description is not repeated. In particular, sometimes the same reference signs are used for the same or similar components to facilitate the understanding.

FIG. 4 shows in a schematic section a third embodiment of the cartridge 100 according to the present invention. In contrast to the first and second embodiments, the storage means 102 containing the liquid 103 is formed by the preferably outer and/or rigid canister 101. The valve 106 is fluidically connected to the storage means 102 preferably via a dip tube 113.

Preferably, the canister 101 is a metallic canister 101, in particular a stainless steel or coated aluminum canister 101.

The cartridge 100 or canister 101 or storage means 102 comprises a gas or air space 104/105 in particular for directly pressurizing the liquid 103.

When the valve 106 is open, the gas or air pressure pushes the liquid 103 out.

The valve 106 is shown in the first and third embodiment as male valve, but can be a female valve as shown in the second embodiment. In this case, the stem 107 can be omitted or formed by a tube or piston 155, the connecting member, the holder 118 or any other part of the inhaler 110.

FIGS. 5 and 6 show a further embodiment of an inhaler 110 (device) according to the present invention for atomising liquid 103, particularly a highly effective pharmaceutical composition or the like, to form an aerosol 116 as shown in FIG. 6.

The inhaler 110 is diagrammatically shown in a tensioned, activated or cocked state (FIG. 5) and in a non-tensioned, non-activated, delivery or discharged state (FIG. 6).

The inhaler 110 is constructed in particular as a portable inhaler and preferably operates without propellant gas. Preferably, the inhaler 110, works only mechanically and/or is hand-held.

The inhalation formulation or liquid 103 is in particular a solution, suspension or suslution (mixture of solution and suspension), but can have any form.

When the inhalation formulation or liquid 103, more particularly a pharmaceutical composition, is nebulised, the aerosol 116 is formed, which can be breathed in or inhaled by a user (not shown). Usually the inhaling is done at least once a day, more particularly several times a day, preferably at set intervals, depending on the complain from which the patient is suffering.

The inhaler 110 has in particular an insertable and preferably exchangeable cartridge 100 containing the liquid 103. The cartridge 100 thus forms a reservoir for the liquid 103, which is to be nebulised. Preferably, the cartridge 100 contains an amount of inhalation formulation or liquid 103 or active substance which is sufficient for multiple doses or uses, in particular to provide up to 200 dosage units, for example, i.e. to allow up to 200 sprays or applications. A typical cartridge 100 holds a volume of about 1 to 15 ml.

The cartridge 100 is preferably substantially cylindrical or cartridge-shaped and once the inhaler 110 has been opened the cartridge 100 can be inserted therein from below and changed if desired. However, the cartridge 100 can also be pre-inserted and/or pre-connected.

Here, the cartridge 100 is preferably similar to the first or second embodiment. In particular, the inhalation formulation or liquid 103 is in particular held in a collapsible storage means 102, here a bellows or bag, in the cartridge 100 or its outer canister 101. The storage means 102 is connected to the valve 106.

The canister 101 or air/gas space 105 is preferably pressurized by air or gas and pressurizes the liquid 103 to the first lower pressure.

The inhaler 110 has a conveying and/or pressurizing means, such as a pump 117, for conveying, metering, pressurizing and/or discharging the inhalation formulation or liquid 103.

In the present embodiment, the inhaler 110 or pump 117 has preferably a holder 118 for the cartridge 100, an associated drive spring 119, only partly shown, with a locking element 120 which can be manually operated to release the spring 119, a conveying and/or connecting member, preferably a conveying tube or piston 155 in particular formed by a thick-walled capillary tube, a non-return valve 121 and/or a pump or pressure chamber 122 (similar to cylinder 157). The inhaler 110 comprises further nozzle 160, in particular a mechanical break-up nozzle, preferably in the region of a mouthpiece 123. A prefilter (not shown) may be arranged stream up the nozzle 160.

The cartridge 100 is fixed or held in the inhaler 110 preferably by the holder 118. The holder 118 may be constructed so that the cartridge 100 is able to be exchanged.

Preferably, the holder 118 or piston 155 or any part or component of the inhaler 110 forms a connecting member for a fluidic connection to the cartridge 100. In particular, the conveying tube/piston 155 may be directly connected with or extend into the valve 106 or its valve member 111.

When the drive spring 119 is axially tensioned the holder 118 with the cartridge 100 and the conveying tube or piston 155 being moved (suction stroke, here downwards in the drawings), the liquid 103 is sucked out of the cartridge 100 into the pressure chamber 122 of the pump 117 through the non-return valve 121. Preferably, the valve 121 is attached to or formed by the conveying tube or piston 155. Then, the inhaler 110 reaches the cocked state shown in FIG. 5.

After actuation of the locking element 120 the inhalation formulation or liquid 103 (not shown) is put under pressure in the pressure chamber 122 as the conveying tube 155 with its now closed non-return valve 121 is moved back upwards by the relaxation of the drive spring 119 and now acts as a pressing ram or piston. This pressure forces the inhalation formulation or liquid 103 through the expulsion or dispensing nozzle 160, whereupon the formulation or liquid 103 is nebulised or atomized into aerosol 116, as shown in FIG. 6.

The tube/piston 155, pump 117, device or inhaler can perform alternately a suction stroke and a pump stroke, also called pressurizing, compression or dispensing stroke. These strokes can be used to control, open and/or close the valve 106. Further, the valve stroke to open/close the valve 106 can be super-imposed.

Preferably the inhaler 110 or pump 117 may have a spring pressure (second higher pressure) of 5 to 200 MPa, preferably 10 to 100 MPa on the liquid 103, which is much higher than the pressure in the cartridge 100, and/or a volume of liquid delivered per stroke of 5 to 100 µl, preferably 10 to 30 µl, most preferably about 15 µl. The liquid 103 is converted into the aerosol 116, the droplets of which have an aerodynamic diameter of up to 20 µm, preferably 3 to 10 µM. The nozzle 160 has preferably a spray angle of 20° to 160°, preferably 80° to 100°.

Preferably, the liquid 103 is pre-pressurized in the cartridge 100 to the first lower pressure and, then, pressurized in the device/inhaler 110 or its pump 117 to the second higher pressure, i.e. in two stages.

Preferably, all liquid 103 is pressurized in two-steps, in particular in the first stage or cartridge 100 to the first (low) pressure of preferably between 1 and 500 kPa or 1 and 200 kPa, in particular between 1 and 100 kPa. Then, preferably only one dose of liquid 103 after the other is pressurized in the second stage or inhaler 110/pump 117 to the second (high) pressure, in particular as mentioned above.

It has to be noted that the cartridge 100 and/or liquid 103 are preferably propellant-free. In particular, the liquid 103 is pressurized in the cartridge 100 by gas or air pressure such that at least essentially no gas or air is outputted together with the liquid 103.

A user (not shown) can inhale the aerosol 116, while an air supply is sucked into the mouthpiece 123 through preferably at least one air supply opening 124, preferably multiple air supply openings 124. Thus, a bypass is formed so that ambient air can be sucked into the mouthpiece 123.

The inhaler 110 comprises preferably an upper housing part 125 and an inner part 126 which is rotatable relative thereto (FIG. 5) having an upper part **126*a* and a lower part 126*b* (FIG. 6), while an in particular manually operable housing part 127 is releasable fixed, particularly fitted onto the inner part 126, preferably by means of a retaining element 128. In order to insert and/or replace the cartridge 100 the housing or lower or bottom part 127 can be detached from the inhaler 110**.

The cartridge 100 is preferably held by the holder 118 or mounted in the inhaler 110 such that the canister 101 is moveable (preferably in lengthwise or axial direction and/or in direction of the back and forth movement of the pump 117 or piston/tube 155) relatively to the connecting member or holder 118 to open and close the valve 106 depending on this relative position. To achieve this relative moveability, the cartridge 100 is held preferably by a bracket-like connection 129, here between a collar 130 and a head 131, so that the relative movement is restricted, in particular to the necessary stroke of valve 106. The collar 130 and head 131 may form part of the cartridge 100 or inhaler 110 or holder 118. In the present embodiment, the holder 118 holds head 131.

It has to be noted that the connection 129 allows an (axial) movement so that the valve 106 can open and close, i.e. the connection 129 allows preferably at least the movement required for the valve storke. In the present embodiment, the connection 129 is integrated into the cartridge 100. However, the connection 129 could also be formed between the cartridge 100 or its canister 101 and the holder 118.

It has to be noted that other constructional solutions are possible. For example, the connecting member or head 131 can be formed by the holder 118 or tube/piston 155 or vice versa.

Preferably, a snap fit is provided to hold the valve ferrule or its stem 107 onto or within the connecting member, tube/piston 155, holder 118 or the like to prevent stem 107 coming out e.g. when inhaler 110 is dropped etc.

In the shown embodiment, the head 131 or tube/piston 155 may form the connecting member for the cartridge 100 or valve 106 to fluidically connect it to the inhaler 110 or pump 117 and may be held by the holder 118. Further, the head 131 or tube/piston 155 may actuate the valve stem 107 or valve member 111 to open and close the valve 106.

FIG. 6 shows the valve 106 in the closed state. The holder 118 or head 131 is spaced from the valve 106 or canister 101 as possible. However, the valve 106 is preferably still fluidically connected to the connecting member, head 131 or tube/piston 155 or inhaler 110 in this state. This facilitates sealing. The cartridge 100 may have an optional return spring 132 biasing the cartridge 100 or head 131 into this state. However, the internal spring 112 of the valve 106 biasing the valve stem 107 or valve member 111 into its closed position may be sufficient. FIG. 6 shows the device or inhaler 110 in the non-activated or discharged or delivery state (after a compression stroke, before the suction stroke), wherein the drive spring 119 is not tensioned, wherein the holder 118 is in its upper position and wherein the valve 106 is closed.

FIG. 5 shows the valve 106 in the open state. The holder 118 or head 131 has been moved towards the valve 106 or canister 101 or vice versa. The valve stem 107 or valve member 111 is depressed. The optional return spring 132 is compressed. This is possible because a means 133 (also called control means) holds or biases the cartridge 100 or canister 101 against the connecting member, tube/piston 155, holder 118 or here upwards or in the axial or stroke direction so that the closing force of the valve 106 and, if spring 132 is provided, the force of spring 132 can be or are overcome. In the present case, means 133 may be a spring or the like. FIG. 5 shows the device of inhaler 110 in the cocked state (at the end of the suction stroke, before the compression stroke), wherein the cartridge 100 has not yet received its end position, but will move a little bit more in the direction of the suction stroke during the closing stroke of valve 106, i.e. until the valve 106 is closed.

The device or inhaler 110 is preferably constructed such that the valve 106 closes or is closed again when the end of the section stroke or the cocked state is reached and/or when the device or inhaler 110 is in the cocked state. In the last case, the valve 106 may close also some time after the cocked state has been reached. The closing of valve 106 is preferred to prevent liquid 103 from leaking out of the cartridge 100 and/or device/inhaler 110, in particular through the nozzle 160, e.g. when the inhaler 110 is not directly used after it has been cocked. In order to achieve the closing of the valve 106 even in the cocked state of the device/inhaler 110, the means 133 may be adapted to reduce or loose its counter-bearing effect or biasing force or counter-force when the cocked state is reached and/or after some time. For this purpose, the means 133 may be formed by a relaxing material, such as a foamed plastic, or by a bellows with a small venting hole or the like as explained in some of the following embodiments.

The control means 133 may be formed by or comprise a spring with a special, in particular non-linear spring characteristic. For example, the spring force may increase until a predetermined position or compression is reached or exceeded and, then, collapse to a reduced force such that the valve 106 closes when only the reduced force acts on the cartridge 100.

Additionally or alternavely, the device on inhaler 110 or control means 133 may be constructed or designed such that the opening of the valve 106 takes place (only) during an over stroke of the device or inhaler 110 or cartridge 100 or canister 101 (in this case, the cartridge 100 or canister 101 or holder 118 has an over stroke in the suction stroke and returns a little bit in the opposite direction when finally reaching the cocked state). Further, the valve 106 may open substantially only when reaching the cocked state or being in the cocked state.

FIGS. 7 and 8 show sectional views of regions of the connection of the cartridge 100 when mounted in the device or inhaler 110, in particular in the inhaler 110 as described in FIGS. 5 and 6. Here, the cartridge 100 is preferably constructed for example according to the second embodiment. The storage means 102 is preferably constructed as a collapsible bag.

In FIGS. 7 and 8, only the holder 118 and the connecting member/conveying tube/piston 155 of the device or inhaler 110 are shown. The other components, such as a housing or the like, have been omitted. FIG. 7 shows the situation similar to FIG. 6, where the valve is closed. FIG. 8 shows the situation similar to FIG. 5, where the valve 106 is open.

The holder 118 or bracket connection 129 may engage or hold the cartridge 100 at a head portion, in particular at the cup 108, preferably in a form-fit manner. In the shown example, arms of the holder 118 or bracket connection 129 engage into a circular groove or any other indention or recess of the cartridge 100, canister 101 or cup 108 as shown. However, these arms can engage also the other indention or groove of the canister 101 adjacent to the spring 112 or can be connected in any other suitable manner.

In the shown embodiment, the connecting member/piston 155 is moveable together with the holder 118 relative to the cartridge 100, canister 101, valve 106 and/or cup 108. During this relative movement, which corresponds to preferably to the valve stroke, the connecting member/piston 155 remains preferably connected to the valve 106 or inserted into valve member 111.

The connection 129 allows movement of the holder 118 and connecting member/piston 155 relative to the cartridge 100/valve 106. In particular, this movement corresponds to or exceeds the stroke of valve 106.

FIG. 7 shows the situation where the holder 118 is moved away or spaced from the cartridge 100/106. In this situation, the valve 106 is closed (the valve member 111 is pressed by spring 112 against sealing 114).

FIG. 8 shows the situation, when valve 106 is opened. Here, the cartridge 100/canister 101/valve 106 on one hand and the holder 118 and/or connecting member/piston 155 on the other hand are moved together. In particular, the holder 118 abuts, e.g. with an abutment surface or protrusion 134 the cartridge 100, canister 101, cub 108 or any part thereof. The connecting member/piston 155 depresses the valve 111 against the force of spring 112. Thus, the valve 106 is opened. The liquid 103 can flow out from the storage means 102 through the valve 106 via the connecting member/piston 155 or the tube 168 formed thereof into the device or inhaler 110. It has to be noted that the valve 106 and piston 155 are not shown filled with liquid 103 in FIGS. 2, 7 and 8.

The closing or biasing force of spring 112 biases the cartridge 100 away from holder 118. Therefore, at least this biasing or closing force has to be overcome, in particular by the control means 133, in order open the valve 106.

As already explained, the cartridge 100 is preferably moveable relative to the connecting member/piston 115 and/or relative to or within the device or inhaler 110, in particular back and forth and/or when operating the pump 117 and/or for opening and/or closing the valve 106.

Preferably, the valve 106 is opened by movement of the cartridge 100 relative to an associated connecting member, such as the piston 155 or the like, and/or within the device or inhaler 110.

Preferably, the device or inhaler 110 comprises the control means 133 for controlling opening and/or closing of the valve 106.

Preferably, the control means 133 acts on a side of the cartridge 100 or canister 101 opposite to the valve 106 or an outlet of the cartridge 100 and/or on a bottom of the cartridge 100 or canister 101.

In particular, the valve 106 is closed between each actuation or use of the device or inhaler 110 or between each dose of dispensed liquid 103.

Preferably, the control means 133 is constructed and/or acts such that its holding, friction or biasing force (which results in an opening of the valve 106 during at least part of the suction stroke and/or in the cocked state) is reduced or omitted before the cocked state is reached, when the cocked state is reached and/or when an position with over stroke is reached and/or after some time.

As already mentioned, the control means 133 may comprise a compression means, in particular an elastic member, such as a piece of foam cellular material foamed plastic, or the like, with the respective characteristics. In the following, some other embodiments of the control means 133 will be explained with reference to the further drawings.

FIG. 9 shows in a schematic section a preferred embodiment of the control means 133 located in the device or inhaler 110, in particular connected to the bottom of bottom part 127. In this embodiment, the control means 133 also comprises a compression means, in particular an elastic member, as already explained. However, the control means 133 comprises or forms alternatively or additionally a damper, in particular an air damper or air cushioning. In particular, the control means 133 comprises a bellows 135 forming the compression means, elastic member and/or damper.

Preferably, the damper acts only in one direction, in particular only during the ssuction stroke and/or acts differently in both (axial) directions of movement or in both strokes.

The compression means or bellows 135 is preferably self-expanding. FIG. 9 shows the bellows 135 in the expanded state. When the bellows 135 is compressed, the air can escape from the bellows 135 via a (small) venting opening 136, in particular a hole formed in an end face, bottom part 137 or the like. The preferably, small cross-section of the venting opening 136 results in a comparatively high force (counter-force) which is required to compress the bellows 135 during the suction stroke and/or when the cartridge 100 is pressed on the damper or bellows 135. This force is higher than the closing force of valve 106 or of spring 112, so that the valve 106 is opened during the suction stroke. When the end position, i.e. the cocked position, is reached by the holder 118 and piston 155, the compressed air in the bellows 135 can further escape via the venting opening 136 so that the force provided by the control means 133 or damper or bellows 135 acting on the cartridge 100 or valve 106 is reduced. This reduced counter-force is lower than the closing force of valve 106 so that the valve 106 closes (slowly) after the holder 118/piston 155 has reached the cocked state or position. Finally, the cartridge 100 or canister 101 reaches an end position by compressing the control means 133 or damper or bellows 135 a little bit further due to the closing force of the valve 106. Thus, the valve 106 closes after the tensioned, activated or cocked state of the device or inhaler 110 has been reached.

When the device or inhaler 110 is used, in particular by pressing or releasing the locking element 120 or releasing the drive spring 119, the cartridge 100 moves in the shown embodiment upwards, i.e. away from the control means 133, and/or follows the pump stroke so that the bellows 135 can expand back into its original position or form, in which it may be pre-compressed or still compressed. Finally, the cartridge 100 is held in the upper position as shown in FIG. 6 with closed valve 106. In this position, the control means 133 or bellows 135 may contact the bottom of the cartridge 100 or not. In particular, the control means 133 or bellows 135 may be constructed or dimensioned such that the valve 106 is opened only during part of the suction stroke and/or substantially only when reaching the cocked state and/or substantially only in the cocked state.

In order to expedite the expansion of the control means 133, the air damper or bellows 135, an aeration valve 138 may be provided. The aeration valve 138 comprises for example a valve element which opens a (large) aeration opening 139 when under pressure occurs in the bellows 135. The valve 138 is preferably a one-way valve and/or automatic valve.

The aeration opening 139 is formed preferably by a hole in the bottom part 137 containing the venting opening 136.

The cross-section of the aeration opening 139 is larger than the cross-section of the venting opening 136 in order to achieve a sufficiently high compression force when compressing the bellows 135 and to achieve a quick expansion of the bellows 135 during the pressure stroke of the device or inhaler 110, i.e. when the cartridge 100 is moved back into its delivery position or into the non-activated position.

The bottom part 127 may comprise a venting hole 140 to allow connection of the openings 136 and 139 to the environment.

FIG. 10 shows a further embodiment of the control means 133. This embodiment is similar to the embodiment according to FIG. 9 so that only mayor differences will be explained. The previous explanations apply in particular in a similar or corresponding manner.

In the embodiment according to FIG. 10, the control means 133 forms also a damper, preferably an air damper or air cushioning. Instead of the bellows 135, the cartridge 100 or its canister 101 or an associated adapter 141 form a piston which cooperates with the device or inhaler 110, in particular with the bottom part 127 or with an cylinder or insert 142. In particular, the adapter 141 is connected to the canister 101 or formed by the canister 101. The adapter 141 or canister 101 forms a piston moveable within the cylinder 142.

In order to achieve a similar function as the embodiment according to FIG. 9 (relatively high compression force to open the valve 106 during the suction stroke and relatively easy expansion or back movement during the pressurizing or pump stroke), the adapter 141 may form a lip, which seals better or more tightly by overpressure and/or during the suction stroke, and which opens or seals less tightly by under pressure or during movement in the opposite direction, i.e. during the pressurizing or pump stroke. Additionally or alternatively, the control means 133 may comprise a (small) venting opening 136, and/or an aeration valve 138 with (large) aeration opening 139 as shown in FIG. 10.

As already mentioned, the function of the control means 133 according to FIG. 10 is similar to the function of control means 133 according to FIG. 9. It has to be noted that the cartridge 100 or its canister 101 move back and forth within the housing or relative to the bottom part 127 when using the device or inhaler 110. Therefore, the piston formed by the cartidge 100 or canister 101 or the adapter 141 moves back and forth as well.

With regard to the embodiments according to FIGS. 9 and 10, it has to be noted that a compression of gas or air results in a counter-pressure and a counter-force which result in the desired opening of the valve 106.

FIGS. 11 to 13 show another embodiment of the control means 133. Here, the valve 106 is opened during a first part of the suction stroke, but closed during a second or last part of the suction stroke and/or when the cocked state is reached.

The control means 133 comprises a preferably metallic control member 145 cooperating with the cartridge 100 or canister 101 or an adapter 143 attached thereto or formed thereof. In the present embodiment, the control number 145 is preferably cage-like or rib-like. In particular, the cartridge 100, canister 101 or adapter 143 comprises or forms a protrusion 114, in particular a nose or the like, which protrudes preferably radially. This protrusion 144 cooperates with a toothing 147 of the control means 143 or control member 145. In particular, the toothing 147 is formed in or by at least one or multiple arms 146 of the control member 147. The toothing 147 is preferably located at the radially inner sides of the arms 146 which are arranged around the cartridge 100, canister 101, adapter 143 or protrusion 144. The toothing 147 is preferably sawtooth-like and/or forms a rathet means.

FIG. 11 shows part of the device or inhaler 110, namely the bottom part 127, with the cartridge 100 in the non-activated or untensioned position. In this position, the cartridge 100 is spaced from the bottom of bottom part 127 and the valve 106 (not shown) is closed.

FIG. 12 shows the cocked state. The cartridge 100 has been moved towards the bottom of bottom part 127, and the valve 106 (not shown) is still open. During the (axial) movement of the cartridge 100 or canister 101 or adapter 103 from the non-activated position shown in FIG. 11 into the cocked or activated position shown in FIG. 12, the protrusion 144 engages or cooperates with the toothing 147 (in particular, the toothing 147 interacts with the protrusion 144 in a ratchet-like manner and/or the toothings 147 or arms 146 (radially) moveable and/or biased against the protrusion 144 such that a friction force or counter-force in the direction of movement, i.e. in axial direction, is generated which overcomes in the closing force of the valve 106 so that the cartridge 100 or canister 101 is moved, biased or pressed against the hole 118 or connecting member or piston 125 and the valve 106 is opened.

Merely at the end of the axial movement into the cocked state, the toothing 147 ends so that the protrusion 144 does not engage with the toothing 147 anymore (this position is shown in FIG. 12). Thus, it can be achieved that the friction force or counter-force of the control means 133 is dropped or reduced. Then, the biasing force of valve 106 can close the valve 106 and move the cartridge 100 or canister 101 a little bit more axially towards the bottom of the bottom part 127.

In the opposite direction, i.e. during the pump stroke, the friction force (provided by the interaction of the toothing 147 with the protrusion 144 in the suction stroke) is preferably reduced or omitted.

The reduction of the friction force in this opposite direction may be achieved by a respective design of the toothing 147 and/or protrusion 144 (e.g. by lesser inclination of the from gliding surfaces of the teeth acting in this direction of movement). Alternatively or additionally, the friction can be reduced by lubrication. This may apply for both directions.

The friction force can be avoided altogether in this opposite direction when the connecting member 145 or the toothing 147 on one hand and the cartridge 100, canister 101, adapter 143 or protrusion 144 on the other hand are rotated (around the longitudinal axis or axis of movement) relative to each other such that the protrusion 144 and the toothing 147 do not interfere during this opposite axial movement. This relative rotation can be achieved for example by respective guiding surfaces on the cartridge 100 or adapter 143 and/or on the control means 133 or control member 145, e.g. such that the cartridge 100 or canister 101 is rotated by a certain angle just before reaching the end position shown in the cocked state and is rotated back by the same angle just before reaching the initial position shown in FIG. 11. However, this rotation or similar rotation of the cartridge 100 or canister 101 can be achieved based on other constructional solutions, e.g. respective guiding surfaces or the like within the device or inhaler 110, e.g. independently on the control means 133 if desired.

FIG. 13 shows a perspective view of the bottom part 127 with the mounted control member 145. In the present embodiment, the control member 145 is preferably rigidly fixed on the bottom of the bottom part 127. However, other constructional solutions are possible as well. In particular, it is also possible to allow a certain rotation of the control member 145 to achieve the desired relative rotation of the toothing 147 to the protrusion 144 as described above. Then, the cartridge 100 or canister 101 can be fixed against rotation.

FIGS. 14 and 15 show another embodiment of the control means 133. FIG. 14 shows in a schematic section a lower part of the device or inhaler 110, namely the bottom 127 with part of the cartridge 100 in the non-activated state. FIG. 15 shows a similar section with the cartridge 100 in the activated or cocked state.

The control means 133 comprises a control member 145 with an inclined guide 148 acting between the control member 145 and the cartridge 100 or canister 101. In the shown embodiment, the guide 148 is formed by an inclined guiding surface 149 of the control member 145 and/or by an inclined guiding surface 150 associated to the cartridge 100.

The inclined guide 148 extents or acts over a certain angle or part of a circumference, preferably the outer circumference of the cartridge 100 or canister 101.

The guide 148 causes that part of the axial downward movement of the cartridge 100 or suction stroke is transformed into a rotational movement of the control member 145. In particular, the control member 145 is held rotationally in the device or inhaler 110, preferably in the bottom part 127, such that the control member 145 can rotate from the position shown in FIG. 14 into the position shown in FIG. 15 against a biasing force, in particular against a spring force provided by a spring (not shown) or the like. The force required to rotate the control member 145 is transformed by the guide 148 in an axial counter-force or vice versa. Thus, an axial counter-force acts on the cartridge 100 when moving axially towards the cocked position as long as the guide 148 acts. This counter-force is higher than the closing force of valve 106 and results in opening of the valve 106.

The guide 148 is designed such that its effect of generating the counter-force is terminated before or when the cocked position is reached. Then, the counter force drops or is reduced such that the valve 106 can close again. During this closing, the cartridge 100 or canister 101 will move a little bit further downwards until the final end position shown in FIG. 15 is reached. In this position, the valve 106 has closed.

In the embodiment described above, the control member 145 is rotatable and the cartridge 100 is secured against rotation. However, it is also possible to realize the same effect when the cartridge 100 is rotatable and the control member 145 is secured against rotation.

The guide 148 guides the relative movement perferably positively and/or forms a crank or connection link or slitted link or the like.

It has to be noted that the cartridge 100 is preferably mounted or mountable or inserted in the device or inhaler 110 and/or connected or connectable to the holder 118 in a predetermined rotational position in the embodiment according to FIGS. 11 to 13 and in the embodiment according to FIGS. 14 and 15.

FIG. 16 shows in a schematic section of a lower part of the device or inhaler 110, in particular of the bottom part 127, a further embodiment of the control means 133. Here, the control means 133 comprises an actuation member 186 which is preferably radially moveable. The actuation member 186 comprises an inclined surface 187 cooperating with the cartridge 100 to convert the (radial) movement of the actuation member 186 into an axial movement of the cartridge 100 to open the valve 106, in particular in the cocked state.

Preferably, the actuation member 186 can be actuated manually when the device or inhaler 110 has been activated or cocked, e.g. drive spring 112 has been tensioned and/or the cocked state has been reached, in order to open the valve 106 in the cocked state. In this cocked state, the actuation member 186 is e.g. radially depressed and, thus, the cartridge 100 or canister 101 is axially shifted upwards against the holder 118, the connecting member and/or piston 155 against the closing force of the valve 106, to open the valve 106.

After release, the closing force of the valve 106 moves the cartridge 100 or canister 101 back downwards into the final end position and, thus, pushes the actuation member 186 back into its initial position.

Preferably, the control means 133 or actuation member 186 is connected or coupled with the device or inhaler 110 or locking element 120 such that the dispensing of a dose of liquid 103 can be triggered, i.e. the locking element 120 depressed and/or the drive spring 119 released, only when the actuation member 186 has been actuated and/or the valve 106 has been opened. The respective coupling of the actuation member 186 with the locking element 120 is not shown in FIG. 16.

According to an alternative embodiment, the valve 106 is constructed such that it has two closing positions. In particular, the valve 106 in a first closing position when the valve stem 107 or valve member 111 is not depressed, and in a second closing position when the valve stem 107 or valve member 111 is depressed completely. The valve 106 opens in between these two end or closing positions, preferably continuously so that the pressure acting in the cartridge 100 can push out the liquid 103 through the valve 106.

The second closing in the second closing position can be realized, e.g. by providing a second valve seat or sealing 188 within the housing 115 below the valve member 111 such that the valve member 111 abuts against this second valve seat or sealing 188 when completely depressed. The second sealing 188 is indicated by a dashed line in FIG. 2, which shows an embodiment of the cartridge 100 according to the present invention. This cartridge 100 can also be used independently from the preferred device/inhaler 110 shown in FIGS. 5 and 6.

Preferably, the valve 106 has a stroke (between the two closing positions) at least substantially equal to the stroke or pump of the device or inhaler 110 or piston 155 or pump 117. Thus, it can be achieved that the valve 106 opens only during the suction stroke and/or pressurizing or pump stroke, but closes in the non-activated state and in the activated or cocked state of the device or inhaler 110.

Preferably, the valve stroke is a little bit smaller than the stroke of the device or inhaler 110 or holder 118 in order compensate any tolerances and ensure secure closing of the valve 106 in both end of positions.

Preferably, any tolerances are compensated by a biasing spring 183 biasing the cartridge 100 or canister 101 against the holder 118.

Preferably, the connection 129 has a stroke which corresponds to the stroke of he valve 106. This leads to the situation that the cartridge 100 can remain more or less unmoved within the device or inhaler 110 during the suction stroke of the pump 117, holder 118, connecting member, piston 155, device or inhaler 110.

The present invention leads to some advantages. It allows a long shelf life of the cartridge 100 and/or inhaler 110. The 1950/60's aerosol technology can be used which is very reliable and not expensive. In particular standard equipment can be used for parts, production and/or filling. Only little or no priming of the inhaler 110 is required. No evaporation takes place during a period of non-use (after the first use or cocking) because there is no (permanent) vent. The cartridge 100 and/or inhaler 110 can be used preferably in any desired orientation, i.e. 360 degree usage is possible.

REFERENCE SIGNS 100 cartridge
101 canister
102 storage means
103 liquid
104 gas or air space
105 gas or air space
106 valve
107 stem
108 cup
109 seal
110 inhaler
111 valve member
112 spring
113 dip tube
114 sealing
115 housing
116 aerosol
117 pump
118 holder
119 drive spring
120 locking element
121 non-return valve
122 pressure chamber
123 mouthpiece
124 opening
125 housing part
126 inner part
126a upper part
126b lower part
127 bottom part
128 retaining element
129 connection
130 collar
131 head
132 return spring
133 control means
134 protrusion
135 bellows
136 venting opening
137 part
138 aerosol valve
139 aeration opening
140 venting hole
141 adapter
142 cylinder/insert
143 adapter
144 protrusion
145 control member
146 arm
147 toothing
148 guide
149 guides surface
150 guiding surface
151 body
152 locking element
154 cover
155 connecting member/piston
157 cylinder
159 spring
160 nozzle
161 ball
162 spring
168 tube
170 valve
183 spring
185 bottom part
186 actuation member
187 inclined surface
188 sealing

The invention claimed is:

1. A device for dispensing or atomizing a liquid (103) containing a medicament, a drug formulation or an inhalation formulation, the device comprising:
   a housing;
   a cartridge (100) comprising: a storage means (102) containing the liquid (103), a valve (106) in fluidic communication with the storage means, and pressurizing means to pressurize the liquid (103) and push the liquid (103) out through the valve (106) when the valve (106) is open;
   a conveying tube (155) having a first end in fluid cooperation with the valve (106) and a second end;
   a pump (117) having a one-way input and piston (121) for receiving the liquid from the second end of the conveying tube and for pressurizing the liquid (103) for delivery after the liquid (103) has passed through the valve (106); and
   a control mechanism (133) for controlling opening and closing of the valve (106), wherein:
   the cartridge (100) is axially movable within the housing between: (i) a first position where the device is in a de-activated state such that: (a) the valve (6) prevents the first end of the conveying tube (155) from being in fluid communication with the liquid within the storage means, and (b) the pump (117) is not ready to pressurize the liquid (103) for delivery, and (ii) a second position where the device is in an activated state such that: (a) the valve (6) permits the first end of the conveying tube (155) to at least temporarily be in fluid communication with the liquid within the storage means, and (b) the pump (117) is ready to pressurize the liquid (103) for delivery, and the control mechanism (133), the valve (106) and the cartridge (100) cooperate such that: (i) the valve (106) is closed and prevents the first end of the conveying tube (155) from being in fluid communication with the liquid within the storage means when the cartridge (100) is in the first position and the device is in the de-activated state, (ii) the valve (106) is open for at least a portion of time and permits the first end of the conveying tube (155) to be in fluid communication with the liquid within the storage means during axial movement of the cartridge (100) from the first position to the second position, and (iii) the valve (106) transitions from opened to closed one of: (a) during the cartridge (100) axial movement from the first position toward the second position, (b) upon the cartridge (100) reaching the second position, and (c) after the cartridge (100) reaches the second position.

2. The device according to claim 1, wherein the storage means (102) is collapsable.

3. The device according to claim 1, wherein the storage means (102) comprises at least one of a bellows and a bag.

4. The device according to claim 1, wherein the pressurizing means comprises at least one of a liquified gas and a permanent gas.

5. The device according to claim 1, wherein the cartridge (100) comprises a gas space (104, 105) as the pressurizing means for pressurizing the liquid (103).

6. The device according to claim 1, wherein the liquid (103) is pressurized in the cartridge (100), wherein the pressure of the liquid (103) is between 1 and 500 kPa.

7. The device according to claim 1, wherein the valve (106) comprises a valve member (111) by which the valve (106) is opened and closed, wherein the valve member (111) is biased into the closed position.

8. The device according to claim 1, wherein the control mechanism (133), the valve (106) and the cartridge (100) cooperate such that the valve (106) is open during axial movement of the cartridge (100) from the first position to the second position, and the valve (106) transitions from opened to closed one of: (a) upon the cartridge (100) reaching the second position, and (c) after the cartridge (100) reaches the second position.

9. The device according to claim 1, wherein the control mechanism (133), the valve (106) and the cartridge (100) cooperate such that the valve (106) is closed during a period in which the cartridge (100) moves from the second position toward the first position and the a pump (117) pressurizes the liquid (103) for delivery.

10. The device according to claim 1, wherein the control mechanism (133), the valve (106) and the cartridge (100) cooperate such that the valve (106) is only open during a suction stroke of the pump (117).

11. The device according to claim 1, wherein the cartridge (100) is coupled to the pump (117) and operates to activate the pump (117) to pressurize the liquid (103) for delivery.

12. The device according to claim 1, wherein the control mechanism (133), operates such that the valve (106) is opened by the movement of the cartridge (100) relative to an associated connecting member within the device.

13. The device according to claim 1, wherein the control mechanism (133) acts on a side of the cartridge (100) that is at least one of: (i) opposite to the valve (106), (ii) opposite to an outlet of the cartridge (100), and (iii) on a bottom of the cartridge (100).

14. The device according to claim 1, wherein the control mechanism (133) comprises a compression mechanism.

15. The device according to claim 1, wherein the control mechanism (133) comprises a damper which is at least one of an air damper and air cushioning.

16. The device according to claim 15, wherein the control mechanism (133) comprises a bellows (135) forming the damper.

17. The device according to claim 15, wherein the cartridge (100) together with at least one of a bottom part (127) and insert (142) of the device forms the damper.

18. The device according to claim 1, wherein the control mechanism (133) comprises at least one of: a control member (145) with variable resistance for the cartridge (100), and a variable counter-force acting on the cartridge (100).

19. The device according to claim 1, wherein an inclined guide (148) of the control mechanism (133) converts the axial movement of the cartridge (100) into a rotational movement of a control member (145) of the control mechanism (133) against a spring force.

20. The device according to claim 1, wherein the control mechanism (133) comprises an actuation member (186) to open the valve (106) in the activated state of the device.

21. The device according to claim 1, wherein the cartridge (100) comprises a sealed outer canister (101) to minimize evaporation of liquid (103) from the storage means (102).

22. The device according to claim 21, wherein the canister (101) is at least one of rigid and made of metal.

23. The device according to claim 1, wherein the cartridge (100) is at least one of pre-inserted into the device and pre-connected to the device or pump (117).

24. The device according to claim 1, wherein the device comprises a non-return valve (121) to which the cartridge (100) is in fluidic communication.

25. The device according to claim 1, wherein the pump (117) comprises a cylinder-piston-arrangement.

26. The device according to claim 1, wherein the device is adapted such that the pressurizing means pressurizes the liquid (103) to a first lower pressure and the pump (117) pressurizes the liquid (103) to second higher pressure.

27. The device according to claim 1, wherein the device meters the liquid (103).

28. The device according to claim 27, wherein the pump (117) pressurizes respective doses of the liquid (103) one after another.

29. The device according to claim 1, wherein the device comprises a nozzle (160) for atomizing the liquid (103) that has been pressurized by the pump (117).

30. The device according to claim 1, wherein at least one of the cartridge (100) and liquid (103) are propellant-free.

31. The device according to claim 1, wherein the device is an inhaler (110).

* * * * *